United States Patent [19]

Powell et al.

[11] 4,313,946
[45] Feb. 2, 1982

[54] **CHEMOTHERAPEUTICALLY ACTIVE MAYTANSINOIDS FROM *TREWIA NUDIFLORA***

[75] Inventors: Richard G. Powell, Peoria; Cecil R. Smith, Jr., Dunlap, both of Ill.

[73] Assignee: The United States of America as represented by the Secretary of Agriculture, Washington, D.C.

[21] Appl. No.: 228,853

[22] Filed: Jan. 27, 1981

[51] Int. Cl.$^3$ .................. A61K 31/535; C07D 498/18
[52] U.S. Cl. ..................... 424/248.54; 260/239.3 P
[58] Field of Search ............................. 260/239.3 P; 424/248.54

[56] References Cited

U.S. PATENT DOCUMENTS 3,896,111 7/1975 Kupchan ........................ 260/239.3
4,225,494 9/1980 Higashide et al. ............... 260/239.3

OTHER PUBLICATIONS

M. C. Wani et al., J.C.S. Chem. Commun., p. 390 (1973).
S. M. Kupchan et al., J. Org. Chem. 42: 2349–2357 (1977).
S. M. Kupchan et al., J. Med. Chem. 21: 31–37 (1978).
E. Higashide et al., Nature 270: 721–722 (1977).
M. Asai et al., Tetrahedron 35: 1079–1085 (1979).
A. G. Galsky et al., Plant Physiol. 65: 184–185 (1980).

*Primary Examiner*—Robert T. Bond
*Attorney, Agent, or Firm*—M. Howard Silverstein; David G. McConnell; Curtis P. Ribando

[57] ABSTRACT

A novel group of maytansinoid compounds has been discovered in the seed tissue of *Trewia nudiflora*. They are represented by the general formula

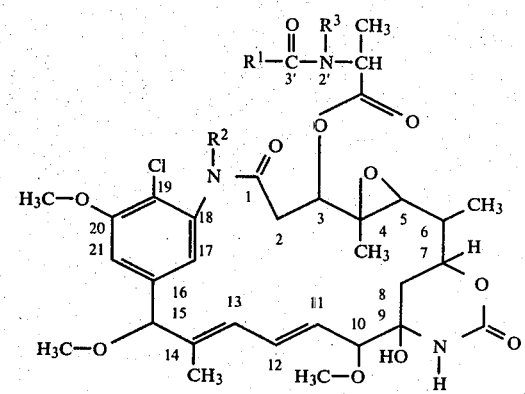

and are all characterized by a distinguishing methoxy group on the C-15 carbon. These isolates have proven to be effective in causing the remission of one or more types of malignancies.

8 Claims, No Drawings

CHEMOTHERAPEUTICALLY ACTIVE MAYTANSINOIDS FROM *TREWIA NUDIFLORA*

CROSS-REFERENCE TO RELATED APPLICATION

This application is related to commonly assigned application Ser. No. 228,852, filed concurrently herewith by Bernard Freedman, Richard G. Powell, and Cecil R. Smith, Jr. entitled "Method of Controlling the European Corn Borer with Trewiasine."

BACKGROUND OF THE INVENTION

1. Field of the Invention

This invention relates to a novel group of ansa macrolide compounds which have utility, inter alia, as chemotherapeutic agents for the remission of malignancies in animals.

2. Description of the Prior Art

The isolation of three ansa macrolides from ethanolic extracts of *Maytenus ovatus* and *Maytenus buchananii* was first reported by S. M. Kupchan et al. and is the subject of U.S. Pat. No. 3,896,111. These maytanside esters are characterized by the structural formula

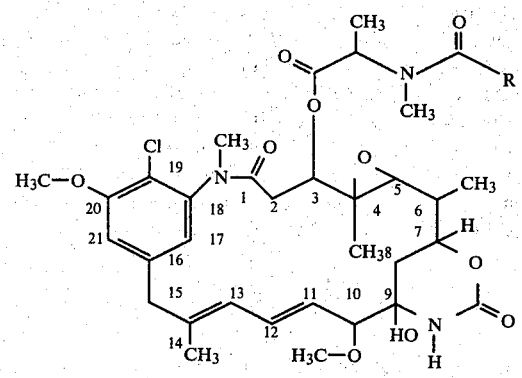

and include maytansine in which $R=CH_3$, maytanprine in which $R=CH_2CH_3$, and maytanbutine in which $R=CH(CH_3)_2$. Kupchan reports that these compounds showed activity against lymphocytic leukemia P388 when administered at a level in the range of 20 to 100 micrograms/kg. of body weight. Two analogs of maytanbutine isolated from *Colubrina texensis* are taught by Wani et al. [J.C.S. Chem. Commun., page 390 (1973)] in which the C-15 position bears either an hydroxyl (colubrinol) or an acetate (colubrinol acetate) side chain. These compounds have also demonstrated activity against lymphocytic leukemia P388 at the microgram per kilogram level, and in addition show cytotoxicity (ED$_{50}$) against KB cell culture at $10^{-4}$–$10^{-5}$ μg./ml. In a later publication by Kupchan et al. [J. Org. Chem. 42: 2349-57 (1977)] a variety of maytansinoids are reviewed and are categorized as either maytanside esters (those having a C-3 ester side chain) or as maytansides (those lacking the C-3 ester side chain). Of particular significance is the disclosure of finding yet another antileukemic principle, maytanbutacine. This maytanside ester was isolated from *Maytenus serrata* and is similar to colubrinol acetate in that it has an acetate side chain in the C-15 position. The difference lies in the C-3 ester group, which is

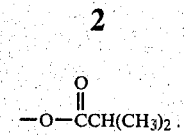

This reference also teaches the isolation of maytansine and related compounds from another celastraceous plant, *Putterlickia verrucosa*.

The significance ascribed to the various structural entities of the maytansinoids for antileukemic activity is discussed by Kupchan et al. [J. Med. Chem. 21: 31–37 (1978)]. Most important for activity is the presence of a C-3 ester, and the particular structure of the ester is also an influencing factor. The C-9 carbinolamide moiety is shown to be critical for optimal activity. In Table II of this publication, the ED$_{50}$ level against KB cell culture of the previously mentioned maytansinoids is shown to be in the range of $10^{-5}$–$10^{-7}$ μg./kg.

Higashide et al. [Nature 270: 721–722 (1977) and U.S. Pat. No. 4,225,494] and Asai et al. [Tetrahedron 35: 1079-85 (1979)] first reported the recovery of ansamitocin, a group of ansamycin antibiotics from a fermentation broth of Nocardia sp. No. C-15003 (N-1). The structures of the compounds are similar to maytansine, differing only with respect to the C-3 moiety. Ansamitocin demonstrated strong growth inhibitory activities against phytopathogenic fungi, dermatophytes, and protozoa. Two of the compounds also possess antitumor activity against the P388 strain at doses as low as 0.8–25 μg./kg. body weight, as well as significant activity against B16 melanoma, sarcoma 180, Ehrlich carcinoma, and P815 mastocytoma. Some activity was also shown against leukemia L1210.

SUMMARY OF THE INVENTION

We have now unexpectedly discovered a novel class of ansa macrolides in the plant tissue of *Trewia nudiflora* L., a heretofore unsuspected maytansinoid source. Galsky et al. [Plant Physiol. 65: 184-5 (1980)] noted that the ethanol extract of this plant possessed activity against crown gall tumors on potato discs, KB cell culture, and P388 leukemia in mice. However, in view of the known occurrence of the maytansinoids in only a relatively few plant species and in only two families, we were surprised to find that this activity was attributed to a group of maytanside esters. We were even more surprised to discover that these compounds were all characterized by a C-15 methoxy substituent unprecedented in any of the previously reported maytansinoids. Hence, this group of compounds is represented by the structural formula

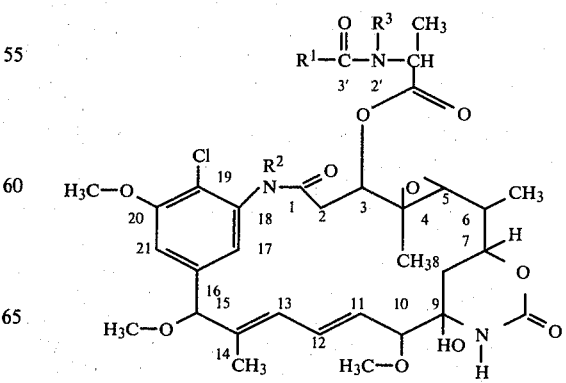

and includes:

trewiasine: $R^1=$—CH(CH$_3$)$_2$, $R^2=$—CH$_3$, and $R^3=$—CH$_3$;

dehydrotrewiasine: $R_1=$

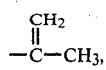

$R^2=$—CH$_3$, and $R^3=$—CH$_3$; and

N-demethyltrewiasine: $R^1=$—CH(CH$_3$)$_2$, $R^2=$—CH$_3$, and $R^3=$—H.

All three of the above-mentioned maytanside esters are active in at least one tumorous test system and at least trewiasine exhibits cytotoxicity at a level of one or more orders of magnitude less than that reported by Kupchan for compounds such as maytansine and maytanbutine.

In accordance with this discovery, it is an object of the invention to provide a novel group of ansa macrolides having utility as chemotherapeutic agents.

It is also an object of the invention to isolate these compounds from the tissue of *Trewia nudiflora*.

A further object of the invention is to prepare chemotherapeutic compositions active against a variety of cancerous disorders.

Another object of the invention is to prepare chemotherapeutic compositions having relatively low cytotoxicity toward the subject organism.

Other objects and advantages of this invention will become readily apparent from the ensuing description.

DETAILED DESCRIPTION OF THE INVENTION

The starting material for use in the invention is the seed of *Trewia nudiflora* L. (Euphorbiaceae), and it is considered likely that other tissues of the plant would also contain extractable quantities of the subject compounds.

The seen material is prepared for extraction by grinding it in a conventional mill to a suitable particle size, usually in the range of about 0.001–3 mm. in diameter, and more preferably in the range of 0.1–2 mm. The ground material is defatted by extraction with a nonpolar solvent such as hexane, followed by extraction with 95% ethanol or similar polar solvent. The extract is separated from the solid residue and is concentrated to remove the bulk of the solvent, at least to the point of reducing the extract to a thin syrup. The resultant concentrate is partitioned between water and a water-immiscible solvent such as chloroform in order to remove the water solubles. By again concentrating the extract so as to eliminate the majority of the solvent, a crude maytansinoid-containing extract is obtained.

Separation and purification of the instant maytanside esters from the crude extract can be effected by the use of the proper combination of conventional techniques including, for example, column chromatography (CC), thin-layer chromatography (TLC), and high-pressure liquid chromatography (HPLC). For isolating trewiasine, we have successfully employed a sequence of operations comprising: (1) CC on silica; (2) HPLC on silica; and (3) HPLC on a reversed phase (C$_{18}$) column. By applying TLC on silica to the appropriate fractions from the second HPLC (operation 3), dehydrotrewiasine and demethyltrewiasine can be separated from one another. While not desiring to be limited thereto, the details of the separation procedure are illustrated by the following example. Fractionation of the ethanolic extract was guided by assay against KB cell culture and PS leukemia in mice.

EXAMPLE

ISOLATION OF COMPOUNDS

A. Approximately 27.2 kg. of *Trewia nudiflora* seed material was ground in a Wiley mill to a particle size of less than about 2 mm. in diameter. The ground material was divided into four batches, each of which was extracted with approximately 32 l. of hexane. A total of 4.07 kg. oil was removed with the hexane fraction, and the four batches of defatted meal were each extracted with approximately 32 l. of 95% ethanol. The extracted residue was discarded and a total of 668 g. of dried material was recovered from the four ethanol fractions. Each fraction was divided in half and partitioned with 1 l. of water and 750 ml. CHCl$_3$ followed by washing the water layer three times with 500 ml. CHCl$_3$. The chloroform fractions and washes from each pair of partitions were combined and taken to dryness and the dried samples representing the four batches were combined into a single crude maytansinoid-containing extract weighing 283.3 g. and identified as F037.

The crude extract (274 g.) was divided in nine portions of approximately 30 g. each and subjected to column chromatography on a column packed with 270 g. of silica. The eluting solvents for each of the nine runs constituted a step-wise gradient of increasing methanol in chloroform, including 1.5 l. CHCl$_3$, 1.5 l. of 5% MeOH in CHCl$_3$, 1.5 l. of 10% MeOH in CHCl$_3$, 1.5 l. of 40% MeOH in CHCl$_3$, and 1.5 l. MeOH. Seven fractions were collected from each run and similar fractions from the nine runs were combined and dried. Activity was highest in the fourth fraction, weighing 32.0 g. and identified as F046.

F046 (30.4 g.) was divided into three portions of approximately 10 g. each and chromatographed on silica by preparative HPLC using a step-wise gradient of increasing methanol in dichloromethane. The eluting solvents for each run included 100 ml. CH$_2$Cl$_2$, 1.5 l. of 2.5% MeOH in CH$_2$Cl$_2$, 1.5 l. of 5% MeOH in CH$_2$Cl$_2$, and 2.0 l. of 10% MeOH in CH$_2$Cl$_2$. Eight fractions were obtained from each run and similar fractions were combined and dried. The highest activity was noted in the fifth fraction, weighing 5.3 g. and identified as F093.

The activity of 389 mg. of F093 was further enriched by preparative HPLC on a reversed phase (C$_{18}$) column eluted with 30% water in methanol. Six fractions were collected, dried, and identified in the order of collection as F097, F098, K099, K100, F101, and F102. K099 (54 mg.) was recrystallized from CH$_2$Cl$_2$ to yield a substantially pure compound having a melting point range of 164°–167° C. and designated as trewiasine. Additional portions of F093 were similarly chromatographed and corresponding fractions of the various runs were combined. A total of 800 mg. trewiasine was collected.

B. F097 (225 mg.) was subjected to HPLC on a reversed phase (C$_{18}$) column eluted with 40% water in methanol. Four fractions were collected and dried, and third of which was designated F109. Likewise, portions of F098 were subjected to HPLC on a reversed phase (C$_{18}$) column eluted with 40% water in methanol. Four fractions were collected and dried, with the second fraction (K104) having the highest activity, and the third fraction (F105) having somewhat less.

3.686 grams of F093, 0.017 g. of F105, and 0.027 g. of F109 were combined, dissolved in $CH_2Cl_2$, and deposited on about 90 cc. of $C_{18}$ silica. The mixture was placed in a precolumn and then subjected to HPLC on a $C_{18}$ prep column eluted with 40% water in methanol. Thirty-one fractions were collected followed by three 1-l. washes with MeOH, $CH_2Cl_2$, and MeOH, respectively. The first MeOH was taken to dryness, and 2.18 g. of the resultant sample was redissolved in $CH_2Cl_2$ and deposited on about 90 cc. of $C_{18}$ silica. This material was placed in a precolumn and then subjected to HPLC on a $C_{18}$ prep column eluted with 2 l. 30% $H_2O$ in MeOH, 2.5 l. 20% $H_2O$ in MeOH, 1 l. 100% MeOH, 1 l. 100% $CH_2Cl_2$, and 1.5 l. 100% MeOH. Of 17 fractions collected, the sixth was taken to dryness, yielding 467.0 mg. of material identified as 11399:39-5.

455 mg. of 11399:39-5 was dissolved in $CH_2Cl_2$ at a concentration of approximately 15 mg./100 μl. and was clarified by passing through a plug of cotton to remove 9 mg. of insolubles. The sample was subjected to HPLC on a $C_{18}$ column and eluted with 30% water in methanol. Of four fractions collected, fraction 3 (11399:41-3) was the largest (333.8 mg.).

All of the material obtained above was dissolved in about 4 ml. $CH_2Cl_2$ and triturated with hexane. After standing overnight, fluffy needles of pure trewiasine (175 mg.) formed having a m.p. of 176°–179° C. and identified as 11399:41-3A. The mother liquor was triturated with more hexane and 133.6 mg. of precipitate was recovered having a m.p. of 173°–178° C. This sample of trewiasine was slightly less pure than the first recovery, and was identified as 11399:41-3B. Finally, the remaining mother liquor was evaporated to dryness and 18.4 mg. of substantially pure trewiasine was recovered and identified as 11399:41-3C. When K104 was treated by preparative TLC, two other fractions, K138 and K135, were obtained. Recrystallization of K138 from $CH_2Cl_2$-hexanes yielded 30 mg. of a dehydrotrewiasine, having a melting point of 165°–170° C.; and likewise, K135 yielded 10–15 mg. of N-demethyltrewiasine, having a melting point of 129°–142°.

CHARACTERIZATION OF COMPOUND STRUCTURES

The structures of the isolated compounds were determined primarily by high resolution mass spectrometry and by proton and carbon 13 NMR using colubrinol and maytansine as standards for comparison. $^1H$ NMR data is given below in Table I and $^{13}C$ NMR is given in Table II. Comparison of the $^1H$ NMR spectra of trewiasine and colubrinol indicated that these two compounds were closely related, the only significant differences being the presence of an additional methoxyl signal at δ 3.37 in the spectrum of trewiasine and an upfield shift of the C-15 proton singlet from δ 5.48 in colubrinol to δ 4.86 in trewiasine. Referring to Table I, the C-15 proton signals of maytansine (m, δ 3.1–3.0 were replaced by the downfield singlet at δ 4.86 in the spectrum of trewiasine, and as shown in Table II, the C-15 carbon signal of maytansine (t, δ 46.60) was shifted downfield in trewiasine (d, δ 86.70). Thus, trewiasine was determined to have the maytansinoid ring system with a methoxyl at C-15. A mass spectrum gave an apparent $M^+ - (H_2O + HNCO)$ at m/e 688.0390 (calcd. 688.3126), confirming that trewiasine was $C_{37}H_{52}ClN_3O_{11}$ (MW=749). Both trewiasine and dehydrotrewiasine give a characteristic ion at m/e 515 ($C_{28}H_{34}ClNO_6$) corresponding to an additional loss of the C-3 substituent as consistent with documented $M^+ - (a+b)$ type maytansinoid fragmentations. Hydrolysis of trewiasine with sodium carbonate in 50% aqueous methanol at room temperature (see Kupchan, J. Org. Chem. 42, supra) gave trewsine, identified by $^1H$ and $^{13}C$ NMR, and N-isobutyryl-N-methylalanine, as determined by GC-MS of the methyl ester. This further confirms the structure of trewiasine to be that of 15-methoxymaytanbutine (15-O-methylcolubrinol).

Dehydrotrewiasine yields a mass spectrum with an apparent $M^{30} - (H_2O + HNCO)$ at m/e 686 indicative of the formula $C_{37}H_{50}ClN_3O_{11}$ (MW=747). This data, together with the $^1H$ and $^{13}C$ NMR data in Tables I and II clearly establishes that dehydrotrewiasine differs from trewiasine only in that it possesses a double bond at the terminal end of the ester side chain.

N-demethyltrewiasine yields a mass spectrum with an apparent $M^+ - (H_2O + HNCO)$ at m/e 674 indicative of the formula $C_{36}H_{50}ClN_3O_{11}$ (MW=735). When the mass spectrometry data is considered in light of the $^1H$ NMR data in Table I, it is evident that this compound distinguishes from trewiasine only by the absence of the amido methyl group.

TABLE I $^1H$ NMR Spectral Data

| Proton assignments | Trewiasine | Dehydrotrewiasine | N-demethyltrewiasine | Maytansine |
|---|---|---|---|---|
| 2 | 2.18 dd | 2.18 dd | 2.18 | 2.16 dd |
| 2 | 2.55 dd | 2.59 dd | 2.55 | 2.60 dd |
| 3 | 4.75 dd | 4.86 dd | 4.84 dd | 4.75 dd |
| 4 $CH_3$ | 0.76 s | 0.80 s | 0.82 s | 0.78 s |
| 5 | 3.01 d | 3.00 d | 2.88 d | 3.00 d |
| 6 $CH_3$ | 1.27 d | 1.28 d | 1.28 d | 1.27 d |
| 7 | 4.28 m | 4.26 m | 4.22 m | 4.26 m |
| 10 | 3.51 d | 3.52 d | 3.52 d | 3.47 d |
| 11 | 5.72 dd | 5.81 dd | 5.73 dd | 5.65 dd |
| 12 | 6.46 dd | 6.47 dd | 6.46 dd | 6.41 dd |
| 13 | 6.98 d | 6.90 d | 6.90 d | 6.65 d |
| 14 $CH_3$ | 1.52 s | 1.52 s | 1.55 s | 1.62 s |
| 15 | 4.86 s | 4.78 s | 4.84 s | 3.10 d |
| 15 | — | — | — | 3.63 d |
| 17 | 6.54 d | 6.64 d | 6.68 d | 6.72 d |
| 21 | 7.22 d | 7.23 d | 7.23 d | 6.81 d |
| 10 $OCH_3$* | 3.35 s | 3.35 s | 3.38 s | 3.33 s |
| 15 $OCH_3$* | 3.37 s | 3.36 s | 3.38 s | — |
| 20 $OCH_3$ | 3.99 s | 3.99 s | 4.00 s | 3.96 s |
| 18 $NCH_3$ | 3.16 s | 3.14 s | 3.14 s | 3.18 s |
| 2' | 5.37 m | 5.29 m | 4.90 m | 5.32 q |
| 2' $CH_3$ | 1.28 d | 1.33 d | 1.35 d | 1.29 d |
| 2' $NCH_3$ | 2.88 s | 2.88 s | — | 2.84 s |
| 4' | 2.76 m | — | 2.30 m | 2.09 s |
| 4' $CH_3$ | 1.06 d | 1.92 s | 1.08 d | — |
| 4' $CH_3$ | 1.12 d | — | 1.16 d | — |
| 5' | — | 5.02 s | — | — |
| 5' | — | 5.22 s | — | — |

*These assignments may be reversed.

TABLE II $^{13}C$ NMR Spectral Data

| Carbon assignments | Trewiasine | Dehydrotrewiasine | Maytansine |
|---|---|---|---|
| Carbonyl, | 176.71 s | 173.33 s | 170.86 s |
| | 170.92 s | 171.96 s | 170.34 s |
| | 168.84 s | 170.47 s | 168.78 s |
| aromatic, | 156.30 s | 156.37 s | 155.91 s |
| | 152.40 s | 152.27 s | 152.34 s |
| and | 142.13 s | 142.00 s | 142.13 s |
| | 141.35 s | 141.48 s | 141.16 s |
| | 139.01 s | 139.99 s | 139.21 s |
| olefinic | 132.51 d | 132.51 d | 133.23 d |
| | 129.92 d | 129.98 d | 127.79 d |
| carbons | 127.97 d | 127.97 d | 125.30 d |
| | 120.30 d | 120.10 d | 122.18 d |
| | 118.93 s | 119.91 s | 118.74 s |

TABLE II-continued

| Carbon assignments | 13C NMR Spectral Data | | |
|---|---|---|---|
| | Trewiasine | Dehydro-trewiasine | Maytansine |
| | 108.96 d | 108.79 d | 113.15 d |
| 2 | 32.43 t | 32.43 t | 32.37 t |
| 3 | 78.18 d | 77.92 d | 78.12 d |
| 4 | 59.99 s | 60.12 s | 60.05 s |
| 5 | 67.73 d | 66.87 d | 67.20 d |
| 6 | 38.86 d | 38.86 d | 38.86 d |
| 7 | 74.15 d | 74.09 d | 74.09 d |
| 8 | 36.26 t | 36.13 t | 36.20 t |
| 9 | 80.72 s | 80.78 s | 80.59 s |
| 10 | 88.52 d | 88.39 d | 88.58 d |
| 15 | 86.70 d | 86.83 d | 46.60 t |
| 2' | 52.38 d | 52.38 d | 52.25 d |
| 4' | 30.42 d | 138.95 s | 21.90 q |
| 4' $CH_3$ | 19.43 q | 20.21 q | — |
| 4' $CH_3$ | 18.85 q | — | — |
| 5' | — | 116.53 t | — |
| 18 $NCH_3$ | 35.22 q | 35.42 q | 35.42 q |
| 2' $NCH_3$ | 30.42 q | 32.43 q | 31.78 q |
| $OCH_3$ | 56.3–7 3q | 56.2–8 3q | 56.61 2q |
| $CH_3$ | 14.62 q | 14.56 q | 15.47 q |
| $CH_3$ | 13.13 q | 13.26 q | 14.56 q |
| $CH_3$ | 11.96 q | 12.22 q | 13.32 q |
| $CH_3$ | 10.01 q | 9.94 q | 12.09 q |

CHEMOTHERAPEUTIC ACTIVITY

The KB Cell Culture Screen used in guiding the above-described fractionations was conducted in accordance with the National Cancer Institute (NCI) Protocol 1.600 [Geran et al., Cancer Chemother. Rep., Part 3, 3:17 (1972)] in which the effectiveness of the test compounds against cultivated cells of human epidermoid carcinoma of the mouth was evaluated. The results of this procedure are expressed as the dose that inhibits growth to 50% of control growth by 3 days after drug addition. Such a dose is referred to as $ED_{50}$ and activity is indicated for $ED_{50}$ levels of $\leq 30$ μg./ml. The smaller the $ED_{50}$ level, the more cytotoxic the test material. The activities of the crystallized compounds isolated above are reported below in Table III.

TABLE III

| KB Activities for Isolated Compounds | | |
|---|---|---|
| Fraction | Compound | $ED_{50}$ μg./ml.) |
| K099 | trewiasine | $2.0 \times 10^{-4}$ |
| K138 | dehydrotrewiasine | $<1 \times 10^{-2}$* |
| K135 | demethyltrewiasine | $<1 \times 10^{-2}$* |

*The actual $ED_{50}$ level was not determined.

Another indication of fraction activity is the effectiveness in the PS system against lymphocytic leukemia P388 in mice. These assays are conducted according to the NCI Protocol 1.200 described in Geran et al., supra. Starting 24 hours after the tumor implantation, previously determined doses of each compound were injected intraperitoneally once a day for 9 days. Survival time of treated leukemic mice is compared to that of untreated mice (T/C×100). A T/C value of 100% indicates no activity. A T/C value greater than 100% means that the treated mice are surviving longer than the control mice. A compound giving a T/C value greater than 125% is indicative of activity as defined by the NCI Protocols, above. The results for the isolated compounds are reported below in Table IV.

Trewiasine was also evaluated in the B1 system against B16 melancarcinoma in mice. This assay is conducted in accordance with the NCI Protocol 1.300 described in Geran et al., supra. Starting 24 hours after the tumor implantation, predetermined doses of the compound were injected intraperitoneally once a day for 9 days. The results are reported in Table V below as the percent T/C.

The above data considered in light of the structural similarity of the subject compounds would collectively suggest a significant probability that all would display similar activity in the three systems tested, as well as in a variety of others.

The expressions "effective amount," "effective dose," and the like as referring to the treatment of animals are defined herein to mean those quantities of maytanside esters which will promote remission of the cancerous growth in the animal to which it is administered, without imparting a toxic response. The effective amount may vary with the injection vehicle, the injection schedule, the sex and species of host, the strain of cancer, and other related factors, all of which may be varied without departing from the scope or operativeness of the invention. In the PS and B1 systems tested, doses on the order of 1–120 μg./kg. body weight/day were generally found to be effective. These levels compare favorably with the activity observed for other maytansinoids, including the ansamitocins. Activity of trewiasine in the KB system is shown to be at least one order of magnitude less than that reported by Kupchan (J. Med. Chem. 21, Table II) for compounds such as maytansine, maytanbutine, maytanprine, and maytanbutacine. It is expected that the activities of dehydrotrewiasine and demethyltrewiasine would be comparable. For this reason, these isolates show potential for displaying fewer side effects in in vivo treatments.

TABLE IV

| PS Activity for Isolated Compounds[1] | | | | | |
|---|---|---|---|---|---|
| Fraction | Compound | Vehicle[2] | Host[3] sex | Dose (μg./kg./inj.)[4] | T/C (%) |
| K099 | trewiasine | M | F | 64.00 | 91 |
| | | | | 32.00 | 128 |
| | | | | 16.00 | 154 |
| | | | | 8.00 | 140 |
| | | | | 4.00 | 163 |
| K138 | dehydro-trewiasine | 2 | M | 32.00 | 145 |
| | | | | 16.00 | 120 |
| | | | | 8.00 | 127 |
| | | | | 4.00 | 120 |

[1] PS evaluation not available for N-demethyltrewiasine.
[2] M = "Klucel" (hydroxypropylcellulose); 2 = biological saline.
[3] All hosts were type $CD_2F_1$ ($CDF_1$) mice.
[4] The doses are reported as micrograms per kilogram of host body weight per injection.

TABLE V

| B1 Activity for Trewiasine | | | | | |
|---|---|---|---|---|---|
| Fraction | Compound | Vehicle[1] | Host[2] sex | Dose (μg./kg./inj.)[3] | T/C (%) |
| K099 | trewiasine | M | M | 32.00 | 183 |
| | | | | 16.00 | 172 |
| | | | | 8.00 | 185 |
| | | | | 4.00 | 157 |
| | | | | 2.00 | 140 |
| | | | | 1.00 | 133 |

[1] M = "Klucel" (hydroxypropylcellulose).
[2] All hosts were type $B_6C_3F_1$ mice.
[3] The doses are reported as micrograms per kilogram of host body weight per injection.

Any pharmaceutically acceptable vehicle or carrier may be used in conjunction with the instant compounds.

It is understood that the foregoing detailed description is given merely by way of illustration and that modification and variations may be made therein without departing from the spirit and scope of the invention.

We claim:

1. A substantially pure compound selected from the group consisting of trewiasine, dehydrotrewiasine, and N-demethyltrewiasine, characterized by the formula

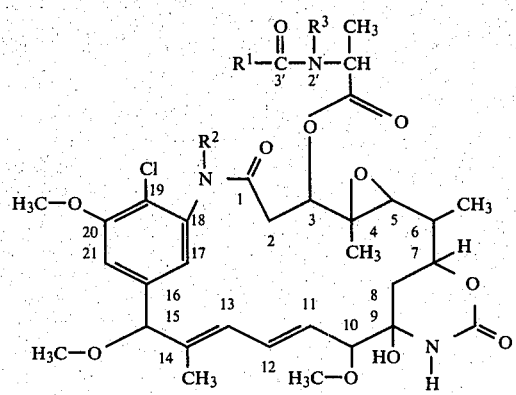

wherein for trewiasine:
$R^1 = -CH(CH_3)_2$, $R^2 = -CH_3$, and $R^3 = -CH_3$;
wherein for dehydrotrewiasine:

$R^1 =$

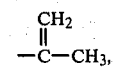

$R^2 = -CH_3$, and $R^3 = -CH_3$; and
wherein for N-demethyltrewiasine:
$R^1 = -CH(CH_3)_2$, $R^2 = -CH_3$, and $R^3 = -H$.

2. The substantially pure compound trewiasine as described in claim 1.

3. The substantially pure compound dehydrotrewiasine as described in claim 1.

4. The substantially pure compound N-demethyltrewiasine as described in claim 1.

5. A chemotherapeutic composition suitable for the remission of leukemia comprising a pharmaceutically acceptable vehicle and an amount effective to promote said remission of a substantially pure compound selected from the group consisting of trewiasine, dehydrotrewiasine, and N-demethyltrewiasine.

6. A composition as described in claim 5 wherein said compound is trewiasine.

7. A composition as described in claim 5 wherein said compound is dehydrotrewiasine.

8. A composition as described in claim 5 wherein said compound is N-demethyltrewiasine.

* * * * *